United States Patent [19]

Kieturakis

[11] Patent Number: 5,624,381
[45] Date of Patent: Apr. 29, 1997

[54] SURGICAL INSTRUMENT AND METHOD FOR RETRACTION OF AN ANATOMIC STRUCTURE DEFINING AN INTERIOR LUMEN

[76] Inventor: Maciej J. Kieturakis, 372 Beverly Dr., San Carlos, Calif. 94070

[21] Appl. No.: 287,580

[22] Filed: Aug. 9, 1994

[51] Int. Cl.⁶ .................................................. A61B 17/00
[52] U.S. Cl. .......................................................... 600/206
[58] Field of Search ...................... 128/20, 4–6; 606/108, 606/152, 153, 197, 191; 600/141, 142, 144, 146, 206

[56] References Cited

U.S. PATENT DOCUMENTS

| | | |
|---|---|---|
| 936,379 | 10/1909 | Stevens . |
| 2,510,198 | 6/1950 | Tesmer . |
| 2,756,752 | 7/1956 | Scherlis . |
| 3,060,972 | 10/1962 | Sheldon . |
| 3,096,962 | 7/1963 | Meijs . |
| 3,190,286 | 6/1965 | Stokes ........................ 600/141 |
| 4,191,191 | 3/1980 | Auburn . |
| 4,334,185 | 6/1982 | Giesy et al. . |
| 4,338,952 | 7/1982 | Augros . |
| 4,535,773 | 8/1985 | Yoon . |
| 4,601,710 | 7/1986 | Moll . |
| 4,654,030 | 3/1987 | Moll et al. . |
| 4,763,662 | 8/1988 | Yokoi . |
| 4,770,163 | 9/1988 | Ono et al. . |
| 4,790,294 | 12/1988 | Allred, III et al. ................ 600/141 |
| 4,836,205 | 6/1989 | Barrett . |
| 4,867,404 | 9/1989 | Harrington et al. . |
| 4,881,537 | 11/1989 | Henning . |
| 5,030,201 | 7/1991 | Palestrant . |
| 5,041,089 | 8/1991 | Mueller et al. . |
| 5,069,679 | 12/1991 | Taheri . |
| 5,116,353 | 5/1992 | Green . |
| 5,147,316 | 9/1992 | Castillenti . |
| 5,147,376 | 9/1992 | Pianetti . |
| 5,179,935 | 1/1993 | Miyagi . |
| 5,190,561 | 3/1993 | Graber . |
| 5,201,325 | 4/1993 | McEwen et al. . |
| 5,203,773 | 4/1993 | Green . |
| 5,209,736 | 5/1993 | Stephens et al. . |
| 5,217,468 | 6/1993 | Clement . |
| 5,224,488 | 7/1993 | Neuffer . |
| 5,224,952 | 7/1993 | Deniega et al. . |
| 5,226,890 | 7/1993 | Ianniruberto et al. . |
| 5,232,451 | 8/1993 | Freitas et al. . |
| 5,258,003 | 11/1993 | Ciaglia et al. . |
| 5,271,380 | 12/1993 | Riek et al. . |
| 5,279,567 | 1/1994 | Ciaglia et al. . |
| 5,284,130 | 2/1994 | Ratliff . |
| 5,312,357 | 5/1994 | Buijs et al. . |
| 5,318,040 | 6/1994 | Kensey et al. . |
| 5,336,237 | 8/1994 | Chin et al. . |
| 5,336,252 | 8/1994 | Cohen . |
| 5,346,504 | 9/1994 | Ortiz et al. . |
| 5,348,541 | 9/1994 | Lyell . |
| 5,368,598 | 11/1994 | Hasson . |
| 5,370,109 | 12/1994 | Cuny . |
| 5,370,647 | 12/1994 | Graber et al. . |
| 5,395,030 | 3/1995 | Kuramoto et al. . |
| 5,441,499 | 8/1995 | Fritzsch . |

Primary Examiner—Michael Powell Buiz
Assistant Examiner—William Lewis
Attorney, Agent, or Firm—Skjerven, Morrill, MacPherson, Franklin & Friel; Norman R. Klivans

[57] ABSTRACT

An instrument and method for retracting an anatomic structure defining a lumen to facilitate an endoscopic procedure in an insufflated workspace. The method includes advancing the distal end of variform intraluminal member in a rigid or semi-rigid linear shape through a lumen in an anatomic structure (e.g., the colon) to the region of an insufflated workspace, making the variform member flexible and retracting the anatomic structure with accessory instruments while the variform member is within the lumen, and then making the variform member rigid in an articulated shape within the lumen to maintain the anatomic structure in the retracted position to facilitate a surgical procedure in the region of the retracted structure.

27 Claims, 4 Drawing Sheets

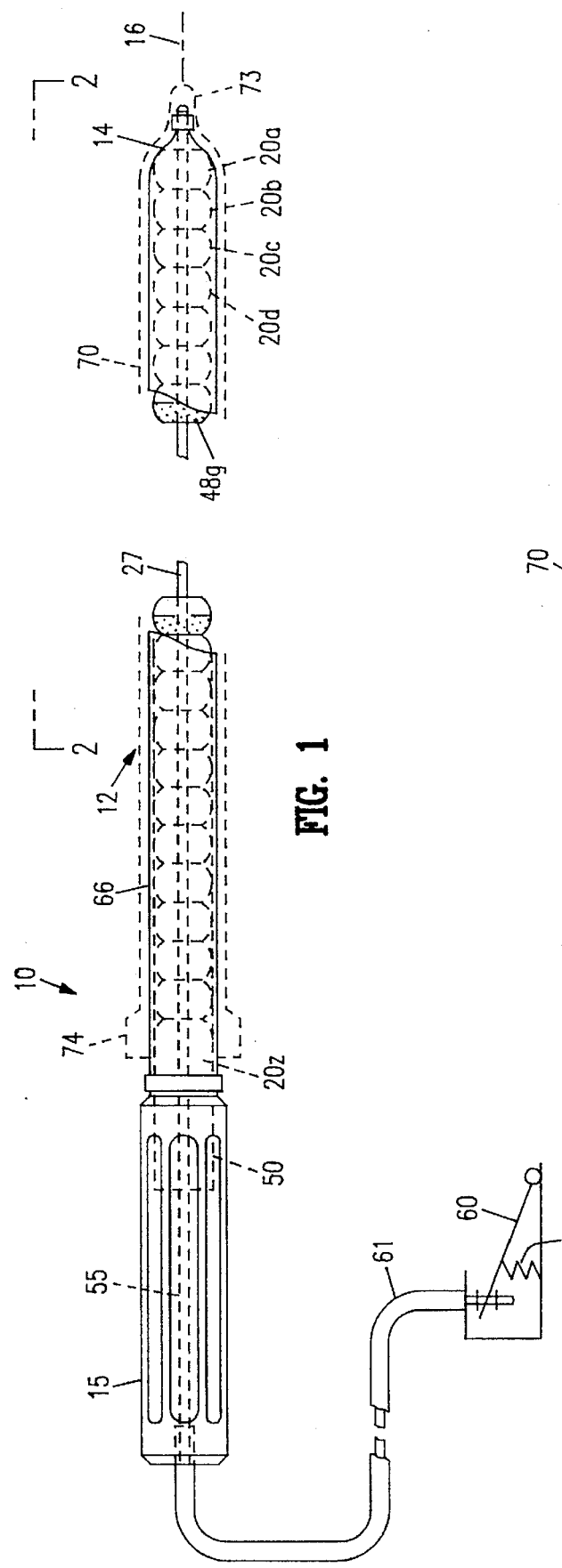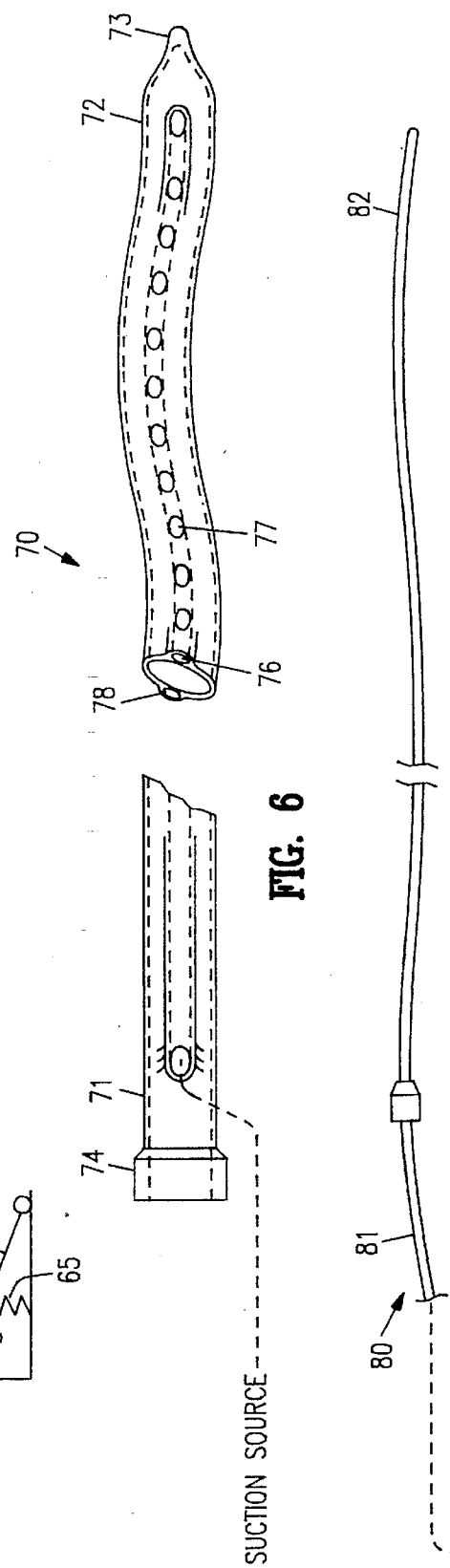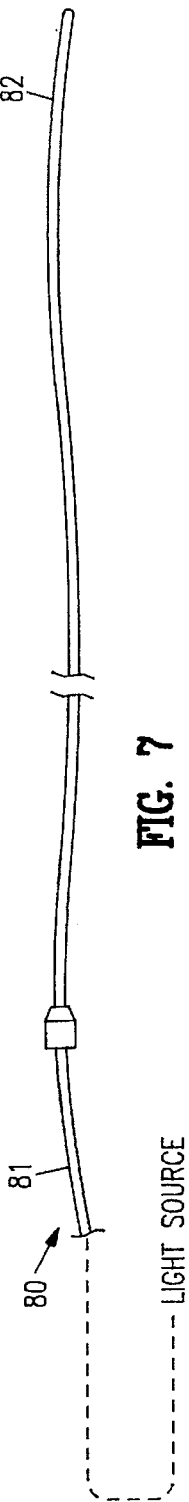

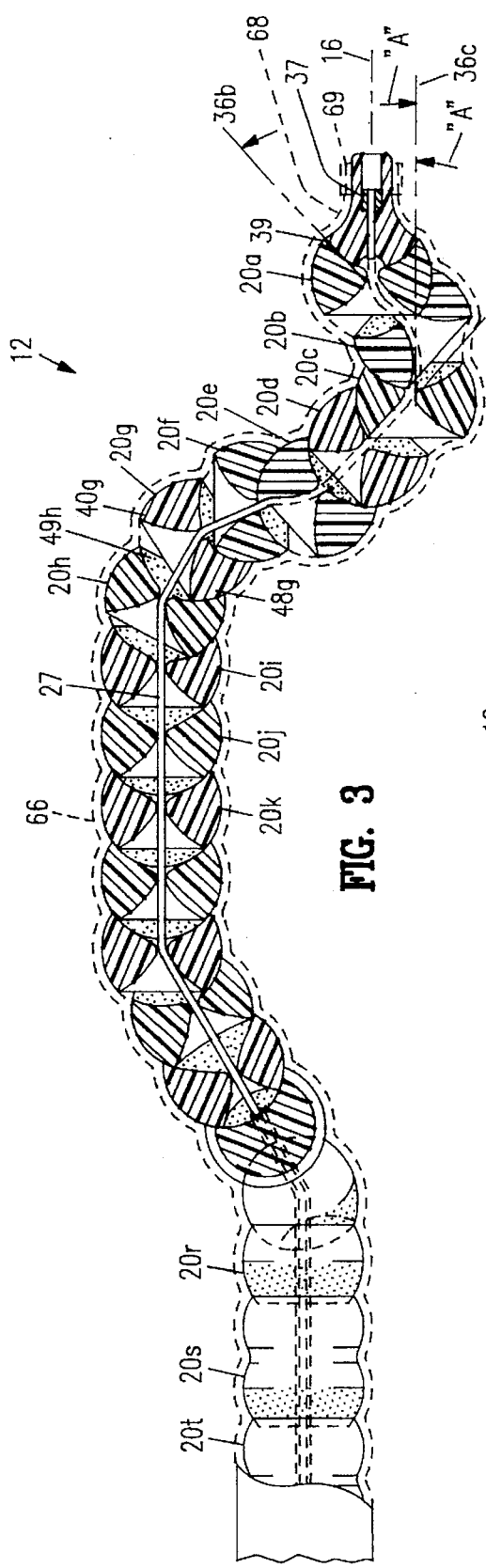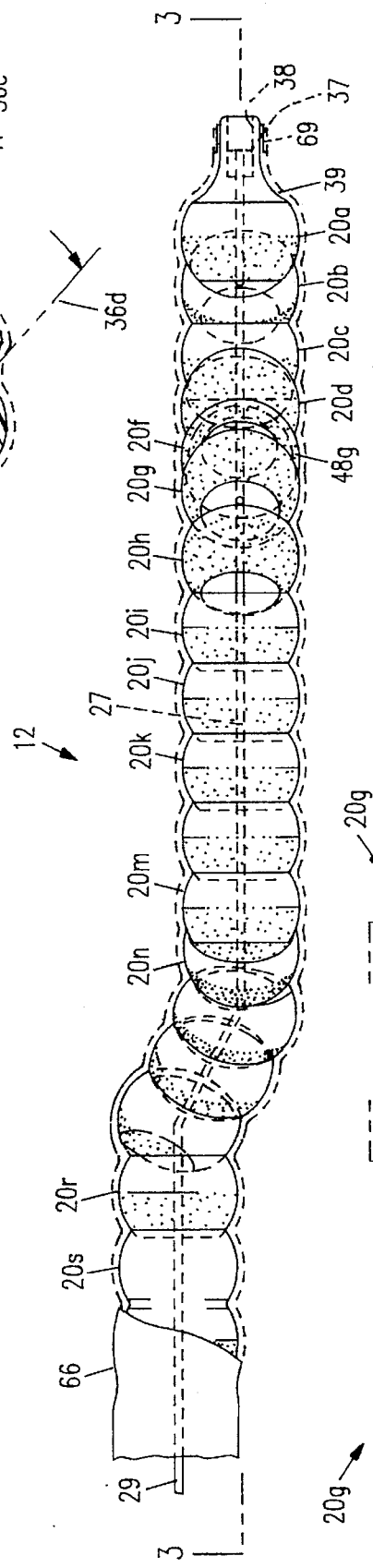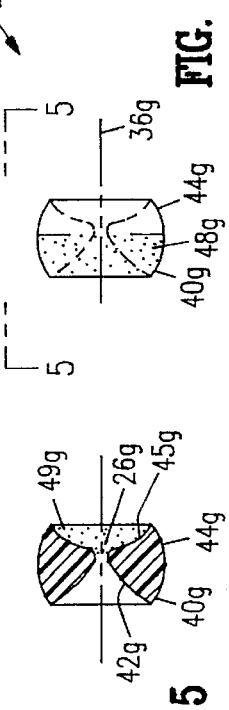

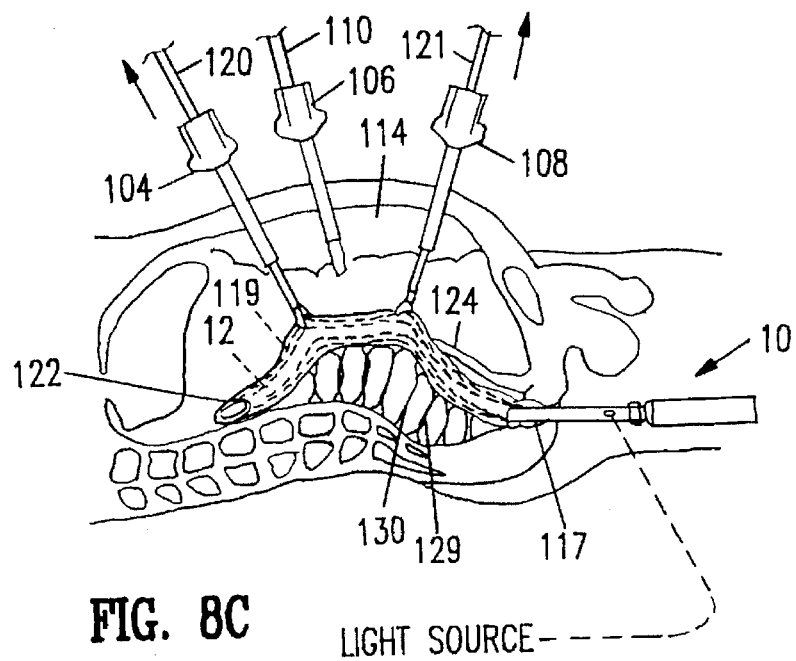
FIG. 8C   LIGHT SOURCE
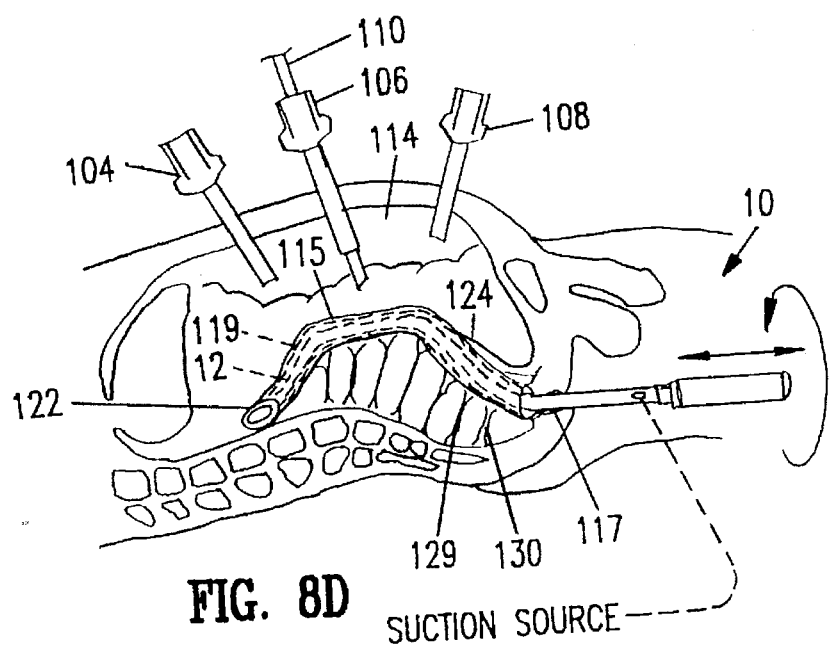
FIG. 8D   SUCTION SOURCE

SURGICAL INSTRUMENT AND METHOD FOR RETRACTION OF AN ANATOMIC STRUCTURE DEFINING AN INTERIOR LUMEN

BACKGROUND OF THE INVENTION

1. Field of the Invention

This invention relates to surgical instrumentation and more particularly to an instrument and method for retracting or repositioning an anatomic structure defining a lumen in an insufflated workspace to facilitate an endoscopic surgery. The invention disclosed herein is related to a co-pending and commonly invented application which is incorporated herein by reference: "Surgical Instrument and Method for Intraluminal Retraction of an Anatomic Structure" filed Jun. 24, 1994, Ser. No. 08/265,577, now U.S. Pat. No. 5,558,665 issued Sep. 24, 1996.

2. Description of Prior Art

In a "minimally invasive" endoscopic surgery in an insufflated abdominal cavity, it has been found that some procedures are complex and time-consuming because of difficulties in retracting or repositioning an anatomic structure with elongate instruments (e.g., graspers). Since all retracting and dissecting instruments are introduced through cannulas that are in stationary positions in the abdominal wall, it often is difficult to retract a structure to access the site of the actual dissection. Often it is necessary to introduce retracting instruments from multiple locations and on occasion, the retracting instruments must cross the region of dissection, obstructing the surgeon's view and interfering with the dissecting instruments. Further, due to its small diameter, an endoscopic retracting instrument cannot apply retraction forces over a broad surface of a structure thus causing retraction forces to be localized to a small surface area which is undesirable. For example, the jaws of a grasper may damage tissue as it grips and pulls on the exterior wall of an anatomic structure.

An illustrative example of a procedure that is difficult to perform endoscopically is a colectomy. Before resecting a portion of the colon, the surgeon must mobilize the colon by dissecting the mesentery that enfolds the colon and also by dividing blood vessels and other connective tissues that adhere to the colon. Utilizing endoscopic graspers as is currently practiced, it is difficult to adequately lift and retract the colon to access all tissues surrounding the colon that must be dissected. The graspers may damage portions of the exterior wall of the colon in regions that are not resected. The surgeon must rely on assistants to handle the retracting instruments while he manipulates the dissecting instruments. Current practice typically requires five cannulas or access ports to accommodate the retracting and dissecting instruments which is an undesirably large number. There is therefore a need for new instruments and methods for retracting an anatomic structure defining a lumen in an insufflated workspace and more particularly for retracting a colon to facilitate a colectomy.

SUMMARY OF THE INVENTION

In general, the instrument and method of the present invention are utilized to "retract" an anatomic structure defining a lumen (cavity) in an insufflated workspace. The terms "retract" and "retraction" herein mean the positioning or repositioning of an anatomic structure in an altered position, or the maintaining of the structure in an altered position or the supporting of the wall of a structure from within its lumen in an initial or altered position.

The instrument in accordance with the present invention includes an elongate variform intraluminal member capable of articulation into many, e.g. an infinite number, of curvilinear shapes and coupled to a handle. The variform member is advanced through the lumen of an anatomic structure to the region of the insufflated workspace. The rigidity of the member is variable, ranging between flexible, semi-rigid and rigid. The variform member includes a plurality of partially mating articulating elements with a flexible tensioning cable extending through the articulating elements. An axial force applied to the tensioning cable causes the articulating elements to frictionally engage one another thus making the variform member rigid in any curvilinear shape. The instrument also incorporates a fiberoptic light source that extends to the distal end of the variform member. The light emitted from the fiberoptic cable will transilluminate tissue from within the lumen of the anatomic structure thus serving as a "locator" which the surgeon can view through an endoscope.

In an exemplary method, assume that the surgeon wishes to retract the sigmoid colon to facilitate a colectomy. Further assume that the patient's abdominal cavity is insufflated and provided with three or more cannulas with an endoscope disposed in one cannula. The surgeon's assistant manipulates the variform member into a substantially linear shape and maintains the linear shape in a rigid or semi-rigid state. The assistant then introduces the variform member into the patient's rectum and advances the member through the sigmoid colon until its distal end reaches the region of the transverse colon. The surgeon views the exterior of the colon through the endoscope which allows him to observe the progress of the variform member within the colon's lumen. The surgeon may observe both "tenting" of the colon wall caused by the variform member as well as transillumination of the colon wall caused by the fiberoptic light source. When the variform member is in the desired position within the colon, the surgeon returns the variform member to it flexible state. The surgeon then endoscopically views the exterior of the colon and utilizes accessory instruments, (e.g., a graspers) to retract and lift the colon to expose the blood vessels and other connective tissues that surround the colon, which articulates the flexible variform member disposed within the colon's lumen. With the colon in the retracted shape, the surgeon then locks the variform member into a rigid articulated shape, thus maintaining the colon in the retracted position by intraluminal support. The surgeon then may withdraw the retracting instruments and introduce dissecting instruments to dissect tissues surrounding to colon to prepare for the resection procedure. The surgeon may cause the colon to be further retracted by manipulating the instrument's handle either axially or rotationally so that the rigid variform member will engage the colon from within its lumen and further reposition the colon.

In general, the present invention provides an instrument and method for retracting a distal anatomic structure defining a lumen. The present invention provides an instrument having a variform intraluminal member capable of being articulated into an infinite number of curvilinear shapes. The present invention is capable of being maintained in a flexible, semi-rigid or rigid state in any curvilinear shape. The present invention also provides a locking mechanism to maintain the variform member in a rigid state in a "hands-free" condition.

The present invention provides an instrument and method that allows for retraction or repositioning of an anatomic structure defining a lumen by applying retraction forces over a broad surface area of the structure, rather than a localized point as with graspers. The present invention also provides a variform member that applies retraction forces from within the lumen of an anatomic structure rather than upon the exterior surface of a structure.

The present invention provides an instrument and method that typically allows for fewer cannulas in an endoscopic surgical procedure because retraction instruments are not needed at the same time as dissection instruments. The present invention also provides an instrument and method in which retracting instruments do not interfere with dissecting instruments since they may not be needed at the same time. The present invention also provides an instrument and method that eliminates the need for a surgeon's assistant to maintain retracting instruments in the retracted position in an endoscopic surgery.

Additional advantages and features of the invention appear in the following description in which several embodiments are set forth.

BRIEF DESCRIPTION OF THE DRAWINGS

FIG. 1 is an elevational view of a device in accordance with the present invention in a linear shape.

FIG. 2 is a partial sectional view of a portion of the variform member of the device of FIG. 1 taken along line 2—2 of FIG. 1 in a non-linear shape.

FIG. 3 is a longitudinal sectional view of a the variform member of FIG. 2 taken along line 3—3 of FIG. 2.

FIG. 4 is an elevational view of an element of the variform member of FIG. 2.

FIG. 5 is a longitudinal sectional view of the element of FIG. 4 taken along line 5—5 of FIG. 4.

FIG. 6 is an elevational view of a sheath to be utilized in conjunction with the device of FIG. 1.

FIG. 7 is an elevational view of a fiberoptic guide that is to be utilized in conjunction with the sheath of FIG. 7.

FIGS. 8A–8D are sagital views of a patient's body illustrating the manner in which the method of the present invention is practiced utilizing the instrument of FIG. 1.

DETAILED DESCRIPTION OF THE INVENTION

Figure 8A:
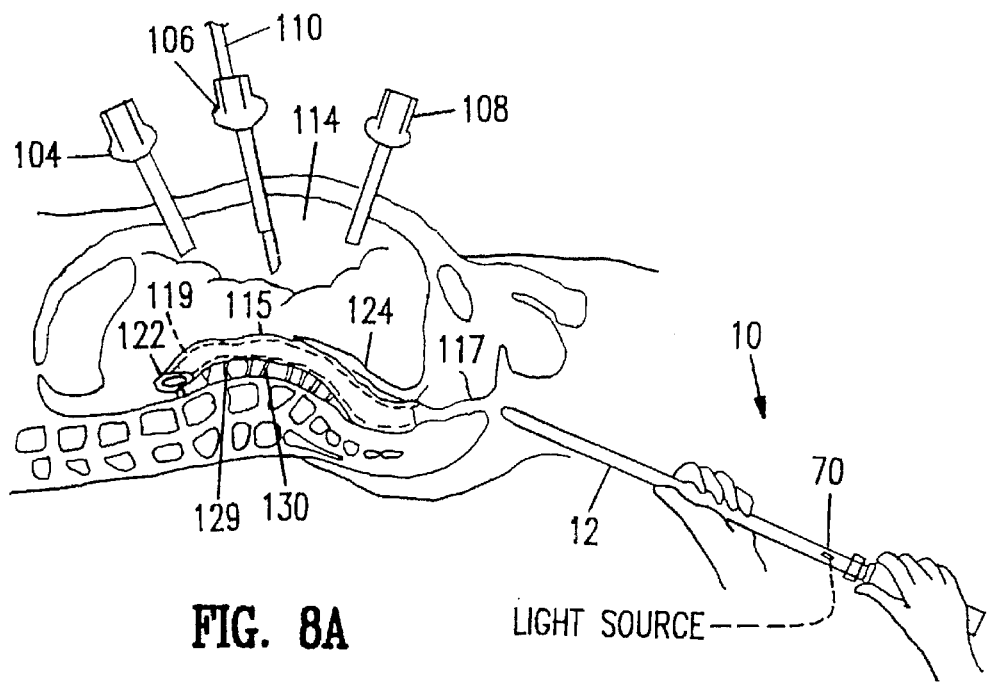

By way of example, FIG. 1 depicts intraluminal retractor 10 with variform intraluminal member 12 that is adapted for retracting the colon of a human patient in a endoscopic colectomy. Variform intraluminal member 12 with proximal and distal ends, respectively 13 and 14, is illustrated in FIG. 1 in a linear shape for introducing into the colon. Variform member 12 has a generally cylindrical sectional shape along longitudinal axis 16 with an overall length of approximately 400 to 600 millimeters (not limiting). The transverse sectional dimension of intraluminal member 12 is approximately 15 mm. to 25 mm. but such dimensions are also not limiting. Referring to FIG. 2, the proximal end 13 of variform member 12 is coupled to a (plastic) cylindrical-shaped handle 15, which is suitable for grasping by the human hand.

Referring to FIGS. 2–3, variform member 12 is an assembly of similar articulating elements, for example elements 20a through 20z, that are made of any suitable material such as plastic. Longitudinal bores 26a–26z extend through each articulating element, 20a–20z, respectively. A tensioning member 27 with a proximal end 28, medial region 29 and distal end 30 is made of e.g. flexible braided stainless steel cable or another suitable material and extends through bores 26a–26z along the axes 36a–36z of the respective articulating elements. The distal end 30 of tensioning member 27 is fixed with crimp nut 37 in counterbore 38 in distalmost tip element 39.

FIGS. 4–5 depict an individual articulating element, for example element 20g. Like the other articulating elements, element 20g has an outer spherical shape with truncated ends and bore 26g extending along axis 36g. In the sectional view of FIG. 5, the proximal face 40g of element 20g is configured with bugle-shaped (flared) recess 42g. The distal face 44g of element 20g is configured with hemispherical recess 45g. As shown in FIG. 4, the proximal face 40g of element 20g has a textured finish such as sandblasted finish 48g. As shown in FIG. 5, the surface of hemispherical recess 45g of element 20g has a similar textured or sandblasted finish 49g.

A mechanism applies axial tensioning forces to tensioning member 27. Referring to FIG. 1, the proximalmost articulating element 20z is fixed in counterbore 50 in handle 15. Handle 15 has axial bore 55 that is aligned with bores, 26a–26z in the articulating elements 20a through 20z. Tensioning member 27 extends through the elements and bore 55. Referring to FIG. 1, a foot pedal 60 is coupled to the proximal end 28 of tensioning member 27 that travels through flexible cable housing 61. Depressing foot pedal 60 causes tensioning member 27 to be pulled in the proximal direction. Spring 65 associated with foot pedal 60 urges the foot pedal to the non-depressed position and thus pushes tensioning member 27 in the distal direction. The foot pedal 60 may be utilized to maintain the tensioning member 27 in a tensioned position either by continuous pressure being applied to the foot pedal or there may be a releasable latch (not shown) incorporated into the foot pedal to maintain the foot pedal in the depressed position.

Referring to FIGS. 2–3, it is useful to describe the application of tensioning forces reference to particular elements, for example elements 20g and 20h. When tensioning member 27 is in a tensioned position as depicted in FIG. 3, proximal face 40g of element 20g is pressed firmly into hemispherical recess 45h of articulating element 20h. The tensioning forces cause the sandblasted surface finishes 48g and 49h of cooperating face 40g and recess 45h, respectively, to frictionally engage one other and to form a substantially rigid interface between the two elements. Such tensioning forces cause a similar frictional engagement between other adjacent articulating elements. In contrast, when tensioning member 27 is in a relaxed or non-tensioned position, the hemispherical faces 40a–40z and cooperating hemispherical recesses 45a–45z along the variform member 12 are not in close frictional contact and tensioning member 27 thus serves as a flexible hinge connection resulting in a flexible variform member. The bugle-shaped recesses, 42a–42z, in the elements allow tensioning member 27 to contour or curve smoothly between the articulating elements in any articulated shape.

The hinge connection between the articulating elements is capable of articulating from 0° to 45° or more between the axes of adjacent elements to form a tight radius in variform member 12. For example, in the articulated shape shown in FIG. 3, each of elements 20b, 20c and 20d is shown articulating at angle "A" (approximately 45°) with respect to its adjacent element as measured by the angles between the respective axes, 36b, 36c and 36d. Similarly, the radial angle between articulating elements may be articulated from 0° to 360° around the respective axes of the elements. Thus, the articulating elements of variform member 12 may be articulated axially and angularly relative to one another to form an infinite variety of curvilinear shapes in three dimensions.

As shown in FIG. 3, variform member 12 may have some articulating elements with an elongate longitudinal shape such as element 20s and 20t resulting in a portion of the variform member that will not deform in as tight a radius as the spherical-shaped elements.

Referring to FIGS. 1–2, outer jacket 66 with proximal and distal ends respectively 67 and 68, is made of any suitable flexible material, for example a thin wall elastomeric tubing such as latex or Tygon R-1000®. When the articulating elements are in a non-tensioned position, the resilient characteristics of the material of jacket 66 may assist in straightening the variform member 12 somewhat for configuring the member in a linear shape for introduction into a lumen in a patient's body. Jacket 66 is fixed over distal end of variform member 12 by metal band 69 compressed over the jacket 66.

FIG. 6 depicts disposable sheath 70 that is adapted to be slipped over intraluminal member 12. Sheath 70 is made of transparent flexible material such a latex and has open proximal end 71 and closed distal end 72 with somewhat tapered tip 73. Gripping collar 74 molded into sheath 70 is adapted for grasping with the fingers to pull the sheath over intraluminal member 12. Open-end channel 76 is incorporated into sheath 70. The diameter of channel 76 may be any suitable dimension, for example from 0.5 mm. to 3 mm. or more and may be used as a vent to relieve fluid pressures that may increase within a lumen in which the variform member is disposed. Channel 76 also may be utilized to deliver therapeutic agents or to apply suction to the interior of a lumen through apertures 77. The apertures 77 may also be disposed around the circumference of sheath 70 to distribute suction evenly within a lumen. Channel 76 also may be utilized as a working channel to introduce a flexible shaft instrument or fiberscope into the lumen through the open distal end.

A similar channel 78 having any suitable dimension is also formed into the exterior of sheath 70. Channel 78 differs from channel 76 in that it has a closed distal end and is adapted to accommodate a fiberoptic light source. FIG. 7 depicts such an optic fiber 80 with proximal and distal ends 81 and 82 that may be disposed within closed-end channel 77 for reasons described hereinbelow. Proximal end 81 may be connected to a conventional light source available in operating rooms for fiberscopes.

Operation and use of the instrument shown in FIG. 1 in performing the method in accordance with the present invention can be described briefly as follows. Assume that the surgeon is to perform an endoscopic colectomy. Retractor 10 is prepared by placing disposable sheath 70 over variform member 12. Optionally, optic fiber 80 may be inserted into closed-end channel 77.

Referring to FIGS. 8A–8D, after conventionally preparing the patient for surgery, the surgeon places three cannula assemblies 104, 106 and 108 (or more) through the abdominal wall and insufflates a workspace, for example using the safety heliscopic cutter disclosed in co-pending application Ser. No. 08/187,753 dated Jan. 26, 1994 now abandoned and the safety trocar disclosed in a co-pending application Ser. No. 08/255,273 filed Jun. 1, 1994 now allowed both incorporated by reference. The surgeon then utilizes endoscope 110 to view around the insufflated space 114 in the region of the sigmoid colon 115 and rectum 117.

Referring to FIG. 8A, the surgeon applies no pressure on foot pedal 60 of FIG. 1 thus relaxing tension forces on tensioning member 27 and the surgeon's assistant grasps retractor handle 15 with one hand and manipulates variform member 12 (exterior to the body) into a relatively linear shape. After the assistant has suitably straightened variform member 12, the surgeon applies pressure on foot pedal 60 which causes tensioning member 27 to be pulled proximally through articulating elements 20a–20z relative to handle 15 and cable housing 61 thus causing variform member 12 to become rigid or semi-rigid depending on the tensioning force applied.

Figure 8B:
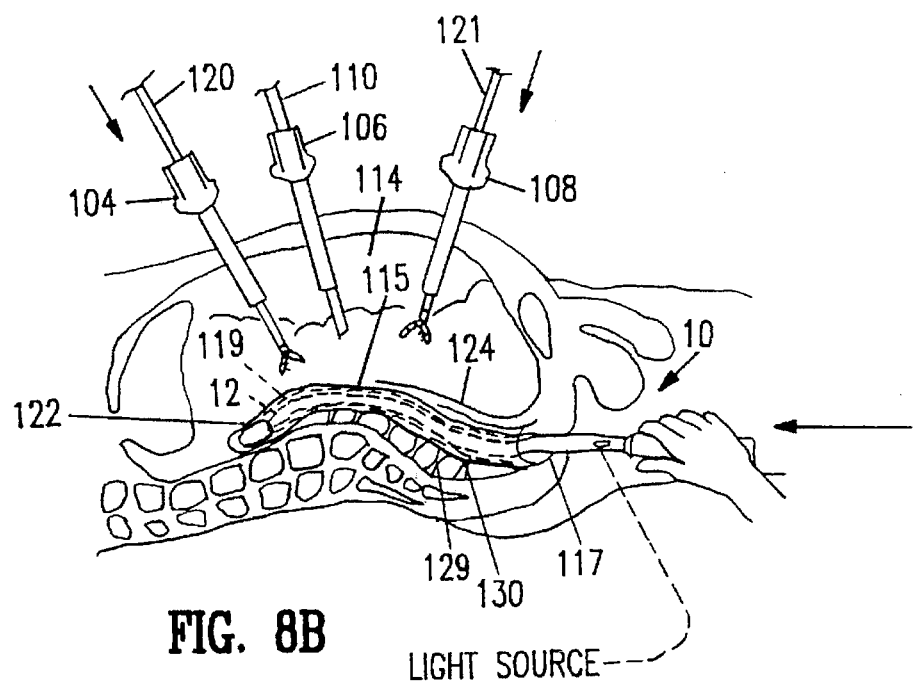

Referring to FIG. 8B, the assistant then introduces variform member 12 through the patient's rectum 117 into lumen 119 in colon 115. The surgeon may view the exterior of colon 115 through endoscope 110 as the assistant advances intraluminal member 12 within the colon. From time to time, the surgeon may slightly release tensioning pressure via the foot petal and re-shape variform member 12 by reshaping the exterior of colon 115 with accessory instruments (e.g., graspers 120 and 121). By again applying tensioning pressure to make the variform member rigid, the assistant may continue advancing the member distally until distal end 14 of variform member 12 is in the region of the transverse colon 122 (see FIG. 8B). The surgeon may locate the distal end 14 of the member by the "tenting" caused by the instrument within the colon and also by the light emitted from distal end 82 of optic fiber 80 that transilluminates the colon wall.

With the variform member advanced to a suitable position as shown in FIG. 8B, the surgeon releases tensioning pressure via foot pedal 60 allowing variform member 12 to assume a flexible state. Still referring to FIG. 8B, the surgeon introduces graspers 120 and 121 through available cannulas. Under endoscopic vision, the surgeon retracts colon 115 away from abdominal walls 122 and mesentery 124 by lifting the colon with graspers 120 and 121. The retraction of the colon articulates the flexible variform member disposed within the lumen. Blood vessels 129 and other connective tissues 130 that adhere between the colon and other structures then are exposed for dissection. With colon 115 in the retracted position as shown in FIG. 8C, the surgeon then utilizes foot pedal 60 to tension the tensioning member 27 thus making variform member 12 fully rigid inside lumen 119 of colon 115. With the intraluminal member again in a rigid state, now articulated within the colon, the surgeon may withdraw graspers 120 and 121 from the insufflated space as shown in FIG. 8D. The colon thus is maintained in the retracted position by the variform member and the surgeon may introduce dissecting instruments through cannulas 104 and 108 to dissect blood vessels 129 and connective tissues 130. During the dissection procedure, at the surgeon's direction, the surgeon's assistant may grasp handle 15 and axially or angularly move the instrument to further retract or reposition the colon to provide better surgical access a particular dissection site. After the colon is thus mobilized, instrument 10 is withdrawn and the resection procedure may follow.

The diameter of variform member 10 fits somewhat loosely in lumen 119 of colon 115. During the above-described procedure, open-end channel 76 incorporated into sheath 70 (see FIG. 6) provides ventilation from the interior of lumen 119 of colon 115 to the exterior of the body and allows gas and other pressures within lumen 119 to be vented thus preventing the colon from becoming distended during the procedure. Optionally, the surgeon may apply a continuous low pressure suction through channel 76. A continuous suction ranging from 20 mm. to 40 mm. Hg. not only will eliminate gas distention pressures, it will shrink pressures of lumen 119 in transverse sectional dimension around variform member 12 to prevent the colon from sliding along the surface of the member. In other words, the suction forces will cause the colon wall to grip and become stable relative to the variform member.

It should be appreciated that a mechanism other than a foot pedal may be used to tension the tensioning member. For example, a pistol-grip handle with a squeeze grip may be suitable. Alternatively, the application of tensioning forces may be reversed with pressure on the foot pedal causing the variform member to assume a flexible state and a lack of pressure on the foot pedal causing the variform member to assume a rigid state.

It should be appreciated that structure other than a tensioning member may be used to cause frictional engagement between articulating members. For example, the articulating elements could be made of a shape memory alloy (SMA) such as a nickel-titanium alloy. An articulating element made from an SMA may be deformed from a heat-stable shape to a heat-unstable shape by application of force. The articulating element exhibits its "shape memory" characteristics by reverting to its heat-stable shape from its heat-unstable shape by application of heat. In a variform member having SMA articulating elements, it would be possible to have a male-female telescoping or nesting interface between the elements that allowed for articulation. In the heat-unstable shape, articulation of the male-female interface would be substantially "loosen" thus providing a flexible variform member. Upon the application of heat, the female portion of an articulating element would revert to its heat-stable shape having a larger transverse sectional dimension which would frictionally engage the fixed-dimension male receiving portion thus providing a substantially rigid variform member.

From the foregoing it can be seen that there is provided an instrument and method that greatly facilitates retraction of anatomic structures defining a lumen, particularly endoscopic procedures. The instrument and method allows the surgeon to retract or reposition the colon with accessory instruments and then to maintain the colon in the retracted position by intraluminal manipulation. It can be readily seen that the variform member of the present invention can be manufactured with other special diameters and embodiments to intraluminally retract and maintain other anatomic structures having a lumen, for example the trachea, esophagus, stomach, duodenum or ureter. Alternative embodiments in small diameters may be used to intraluminally retract structures such as veins and arteries. It should be appreciated that an intraluminal retractor for such applications may range in diameter from e.g. 1 mm. or less to 40 mm. or more and have any required length to accomplish a particular retraction.

This disclosure is illustrative and not limiting. Further variations will be apparent to one skilled in the art in light of this disclosure and are intended to fall within the scope of the appended claims.

I claim:

1. A surgical instrument for retracting an anatomic structure in a body, the anatomic structure defining a lumen, comprising:

an elongate member having a proximal portion and a distal portion and defining an axis extending therebetween, wherein the elongate member is capable of articulation into a substantially linear shape for introduction into the lumen and a plurality of curvilinear shapes for retracting the anatomic structure surrounding the lumen;

a tensioning member incorporated into and coupled to the elongate member, wherein the elongate member is in one of a tensioned and non-tensioned positions dependent on tension provided by the tensioning member; and a tensioning structure connected to a proximal end of the elongate member and to the tensioning member, thereby allowing the tensioning member to be in one of the tensioned and non-tensioned positions.

2. The device of claim 1, wherein the tensioning structure is capable of maintaining the elongate member substantially rigid in the tensioned position.

3. The device of claim 1, wherein the tensioning structure is capable of maintaining the elongate member substantially flexible in the non-tensioned position.

4. The device of claim 1, wherein the tensioning structure is capable of maintaining the elongate member between being substantially rigid and substantially flexible.

5. The instrument of claim 1, wherein the elongate member includes a plurality of cooperating longitudinal elements each defining a cooperating longitudinal bore extending therethrough, together with the tensioning member slidably disposed in each bore, each longitudinal element having a first end and a second end with respective first and second abutting surfaces for abutting an adjacent longitudinal element, whereby tensioning of the tensioning member causes the abutting surfaces to frictionally contact one another.

6. The instrument of claim 5, wherein the first and second abutting surfaces include respectively a protruding form and a recessed form, the forms each telescopically mating with an abutting longitudinal element.

7. The instrument of claim 6, wherein the protruding and recessed forms each have a partly spherical shape.

8. The instrument of claim 5, wherein the first and second abutting surfaces have a textured surface, thereby enhancing frictional contact between abutting longitudinal elements.

9. The instrument of claim 5, wherein the first and second abutting surfaces in a portion of the elongate member have a surface that is not textured, thereby reducing frictional contact between abutting longitudinal elements.

10. The instrument of claim 1, wherein the elongate member includes a plurality of cooperating longitudinal elements, each longitudinal element having a first end and a second end and including a respective protruding form and a recessed form, the forms each telescopically mating with an abutting longitudinal element, each longitudinal element being of a shape-memory alloy.

11. The instrument of claim 1, wherein the elongate member defines an interior channel for accommodating optic fibers and extending from the proximal portion of the elongate member to the distal portion thereof.

12. The instrument of claim 1, wherein the elongate member defines a longitudinal interior channel with open proximal and distal ends.

13. The instrument of claim 1, wherein the elongate member includes a suction source for applying suction through a channel, thereby to apply suction to an exterior of the distal portion of the elongate member.

14. A surgical method for retracting an anatomic structure in a body defining a lumen, utilizing an elongate member that is articulatable between a substantially linear shape and a plurality of non-linear shapes and alterable between being rigid and flexible, the method comprising the steps of:

adjusting the elongate member to the substantially linear shape;

maintaining the elongate member at least partly rigid while being in the linear shape;

introducing the elongate member into a first location in the lumen;

advancing the elongate member within the lumen to a second location in the lumen;

altering the elongate member to be flexible and maintaining the elongate member flexible;

manipulating the anatomic structure defining the lumen from an exterior of the anatomic structure, thereby articulating the flexible elongate member within the lumen to an articulated shape; and altering the elongate member to be rigid and maintaining the elongate member rigid in the articulated shape, thereby retracting the anatomic structure.

15. The method of claim 14, wherein the introducing step includes introducing the elongate member into the lumen through an end of the lumen.

16. The method of claim 14, wherein the introducing step includes introducing the elongate member into the lumen through an incision in a wall of the anatomic structure.

17. The method of claim 14, further comprising the step of illuminating a wall of the anatomic structure surrounding the lumen by a light source associated with a distal portion of the elongate member.

18. The method of claim 14, further comprising the step of manipulating the elongate member while rigid, thereby further retracting the anatomic structure.

19. A surgical method for mobilizing a patient's colon utilizing an elongate member articulatable between a substantially linear shape and a plurality of non-linear shapes, comprising the steps of:

adjusting the elongate member to a substantially linear shape;

maintaining the elongate member in an at least partly rigid state;

introducing the elongate member through the patient's rectum into the colon;

altering the elongate member to a flexible state and maintaining the elongate member in the flexible state;

manipulating an exterior of a portion of the colon through at least one incision in an abdominal wall of the patient, thereby articulating the elongate member to an articulated shape;

altering the elongate member to a rigid state and maintaining the elongate member in the rigid state in the articulated shape, thereby retracting the portion of the colon; and dissecting tissues adhering to the portion of the colon, thereby mobilizing the portion of the colon.

20. The method of claim 19, further comprising prior to the introducing step, the steps of:

placing a plurality of sleeves in the patient's abdominal wall;

insufflating the patient's abdominal cavity, thereby providing a workspace;

introducing an endoscope through a first of the sleeves into the workspace; and viewing the portion of the colon through the endoscope;

wherein the manipulating step includes manipulating the exterior of the portion of the colon by at least one instrument introduced through a second of the sleeves.

21. The method of claim 19, further comprising contemporaneous with the introducing step, the steps of:

transmitting a light to the distal portion of the elongate member through an interior channel in the variform member, thereby illuminating a part of the wall of the colon; and observing endoscopically the illuminated part of the wall the colon from the exterior of the colon.

22. The method of claim 19, further comprising subsequent to the introducing step, the step of:

applying a suction through a channel of the elongate member to an interior of the colon, thereby preventing the colon from distending.

23. A surgical method for retracting a wall surrounding a lumen in an organ, utilizing an elongate member articulatable between a substantially linear shape and at least one non-linear shape and alterable between being rigid and flexible, comprising the steps of:

introducing the elongate member into a first location in the lumen in a substantially linear shape while the elongate member is at least partly rigid;

advancing the elongate member within the lumen to a second location in the lumen while being in the linear shape;

altering the elongate member to be flexible;

articulating the flexible elongate member to a non-linear shape and then maintaining the non-linear shape rigid, thereby retracting the wall surrounding the lumen by applying retraction along an interior of the wall.

24. A surgical instrument for retracting an anatomic structure in a body, the anatomic structure defining a lumen, comprising:

an elongate member having a proximal portion and a distal portion and defining an axis extending therebetween, wherein the elongate member is capable of articulation into a substantially linear shape for introduction into the lumen and a plurality of curvilinear shapes for retracting the anatomic structure surrounding the lumen;

a tensioning member incorporated into and coupled to the elongate member; and a tensioning structure connected to a proximal end of the elongate member and to the tensioning member, thereby actuating the tensioning member; wherein the elongate member includes a plurality of cooperating longitudinal elements each defining a cooperating longitudinal bore extending therethrough, together with the tensioning member slidably disposed in each bore, each longitudinal element having a first end and a second end with respective first and second abutting textured surfaces for abutting an adjacent longitudinal element thereby enhancing frictional contact between abutting longitudinal elements, whereby tensioning of the tensioning member causes the abutting surfaces to frictionally contact one another.

25. A surgical instrument for retracting an anatomic structure in a body, the anatomic structure defining a lumen, comprising:

an elongate member having a proximal portion and a distal portion and defining an axis extending therebetween, wherein the elongate member is capable of articulation into a substantially linear shape for introduction into the lumen and a plurality of curvilinear shapes for retracting the anatomic structure surrounding the lumen;

a tensioning member incorporated into and coupled to the elongate member; and a tensioning structure connected to a proximal end of the elongate member and to the tensioning member; wherein the elongate member includes a plurality of cooperating longitudinal elements, an end of each longitudinal element mating with an end of an abutting longitudinal element, each longitudinal element being of a shape-memory alloy.

26. A surgical instrument for retracting an anatomic structure in a body, the anatomic structure defining a lumen, comprising:

an elongate member having a proximal portion and a distal portion and defining an axis extending therebetween, wherein the elongate member is capable of articulation into a substantially linear shape for introduction into the lumen and a plurality of curvilinear shapes for retracting the anatomic structure surrounding the lumen;

a tensioning member incorporated into and coupled to the elongate member; and a tensioning structure connected to a proximal end of the elongate member and to the tensioning member; wherein the elongate member includes a suction source for applying suction through a channel in the elongate member, thereby to apply suction to an exterior of the distal portion of the elongate member.

27. A surgical method for retracting an anatomic structure in a body defining a lumen, utilizing an elongate member that is articulatable between a substantially linear shape and a plurality of non-linear shapes, the method comprising the steps of:

adjusting the elongate member to the substantially linear shape;

maintaining the elongate member in at least partly rigid state;

introducing the elongate member through an incision in a wall of the anatomic structure into a first location in the lumen;

advancing the elongate member within the lumen to a second location within the lumen;

altering the elongate member to be flexible and maintaining the elongate member flexible;

manipulating the anatomic structure defining the lumen from an exterior of the anatomic structure, thereby articulating the elongate member within the lumen to an articulated shape;and altering the elongate member to be rigid and maintaining the elongate member rigid in the articulated shape, thereby retracting the anatomic structure.

* * * * *